US00PP30873P3

(12) United States Plant Patent
Georgusis

(10) Patent No.: US PP30,873 P3
(45) Date of Patent: Sep. 3, 2019

(54) ***PHLEBOSIA* HYBRID PLANT NAMED 'NICOLAS DIAMOND'**

(50) Latin Name: ***Phlebodium aureum* (L.) J. Sm. x *Pyrrosia lingua* (Thunb.) Farw.**
Varietal Denomination: Nicolas Diamond

(71) Applicant: Vitro Plus, B.V., Burgh-Haamstede (NL)

(72) Inventor: James Georgusis, Metaire, LA (US)

(73) Assignee: Vitro Plus, B.V., Burgh-Haamstede (NL)

( * ) Notice: Subject to any disclaimer, the term of this patent is extended or adjusted under 35 U.S.C. 154(b) by 0 days.

(21) Appl. No.: 16/350,243

(22) Filed: Oct. 17, 2018

(65) Prior Publication Data

US 2019/0116710 P1 Apr. 18, 2019

(30) Foreign Application Priority Data

Oct. 17, 2017 (QZ) ..... PBR 2017/2597

(51) Int. Cl.
*A01H 5/12* (2018.01)
*A01H 9/00* (2006.01)

(52) U.S. Cl.
USPC ..... Plt./379
CPC ..... *A01H 9/00* (2013.01)

(58) Field of Classification Search
USPC ..... Plt./373, 379
See application file for complete search history.

(56) References Cited

PUBLICATIONS

Hortipoint: Flower Trials: Vitro Plus is developing a new type of sailing. Jun. 28, 2018. https://www.hortipoint.nl/vakbladvoordebloemisterij/vitro-plus-ontwikkelt-nieuw-type-varen/. 2 pages. (Year: 2018).*

* cited by examiner

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

A new and distinct x *Phlebosia* cultivar named 'Nicolas Diamond' which is characterized by a fast rate of growth, improved cold hardiness and drought tolerance, with dark green pinnatifid leaves which are curled downward toward the apex, and the stability of these characteristics from generation to generation.

3 Drawing Sheets

Latin name of the genus and species: The Latin name of the genus and species of the novel variety disclosed herein is *Phiebodium aureum* (L.) J. Sm. x *Pyrrosia lingua* (Thunb.) Farw., also known as x *Phlebosia*.

Variety denomination: The inventive variety of x *Phlebosia* disclosed herein has been given the variety denomination 'Nicolas Diamond'.

CROSS REFERENCE TO RELATED APPLICATIONS

This application claims priority to the Community Plant Variety Rights application number 2017/2597, filed Oct. 17, 2017, which is herein incorporated by reference.

BACKGROUND OF THE INVENTION

Parentage: 'Nicolas Diamond' is a seedling selection which resulted from the open pollination of *Phiebodium aureum* 'Mandaianum' (unpatented), the seed parent, with *Pyrrosia lingua* 'Cristata' (unpatented), the pollen parent. In 2016 the inventor discovered the seedling at his greenhouse in Metaire, La. The seedling was initially noted for its unique foliage habit and fast rate of growth and was isolated for further observation in order to confirm the distinctness and stability of the characteristics first observed. After further evaluation it was determined that the unique characteristics of the candidate plant would prove favorable for commercial marketability. The new variety was given the breeder denomination 'Nicolas Diamond'.

Asexual Reproduction: Asexual reproduction of the new cultivar 'Nicolas Diamond', by way of mericloning, was first initiated in 2016 at a laboratory in Metaire, La. Through four subsequent generations, the unique features of this cultivar have proven to be stable and true to type.

SUMMARY OF THE INVENTION

The cultivar 'Nicolas Diamond' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Nicolas Diamond'. These characteristics in combination distinguish 'Nicolas Diamond' as a new and distinct x *Phlebosia* cultivar:

1. x *Phlebosia* 'Nicolas Diamond' exhibits a fast rate of growth; and
2. x *Phlebosia* 'Nicolas Diamond' exhibits improved cold hardiness and drought tolerance; and
3. x *Phlebosia* 'Nicolas Diamond' exhibits dark green, deeply lobed, pinnatifid leaves which are curled downward toward the apex.

BOTANICAL DESCRIPTION OF THE PLANT

Figure 1:
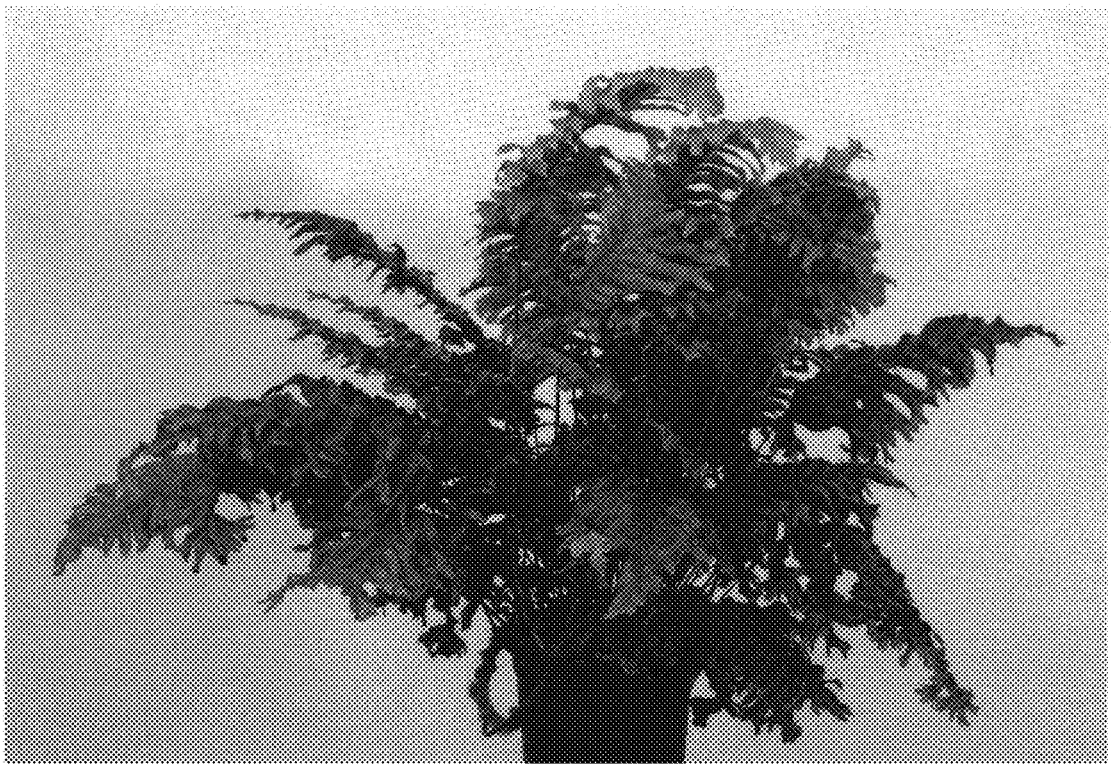
FIG. 1 illustrates, as nearly true as it is reasonably possible to make the same in color photographs of this type, an exemplary plant of 'Nicolas Diamond' grown in a commercial greenhouse in Burgh Haamstede, the Netherlands. This plant is approximately 24 month old, shown planted in a 17 cm container.
Figure 2:
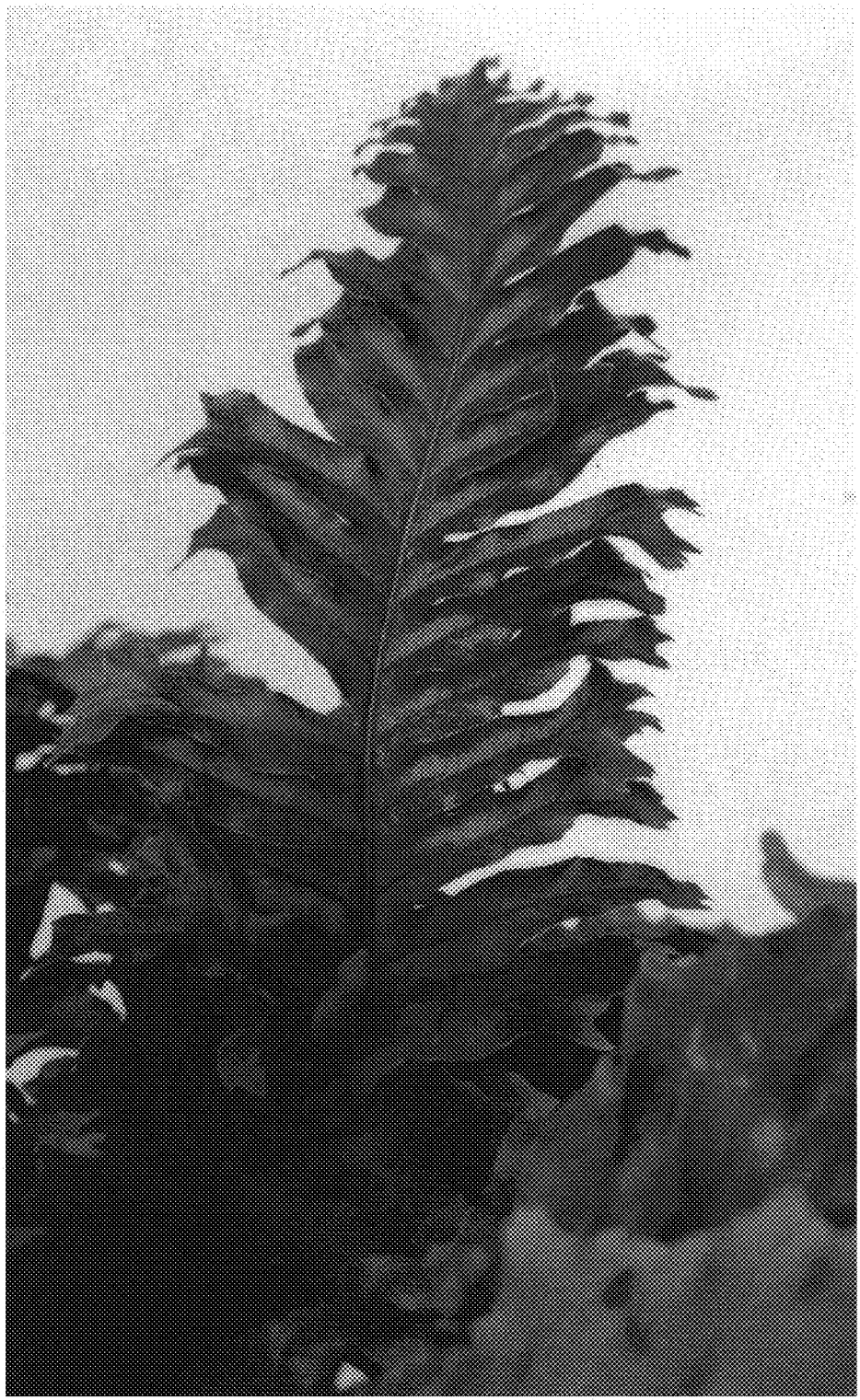
FIG. 2 illustrates, as nearly true as it is reasonably possible to make the same in color photographs of this type, the typical apical foliage habit of 'Nicolas Diamond'.
Figure 3:
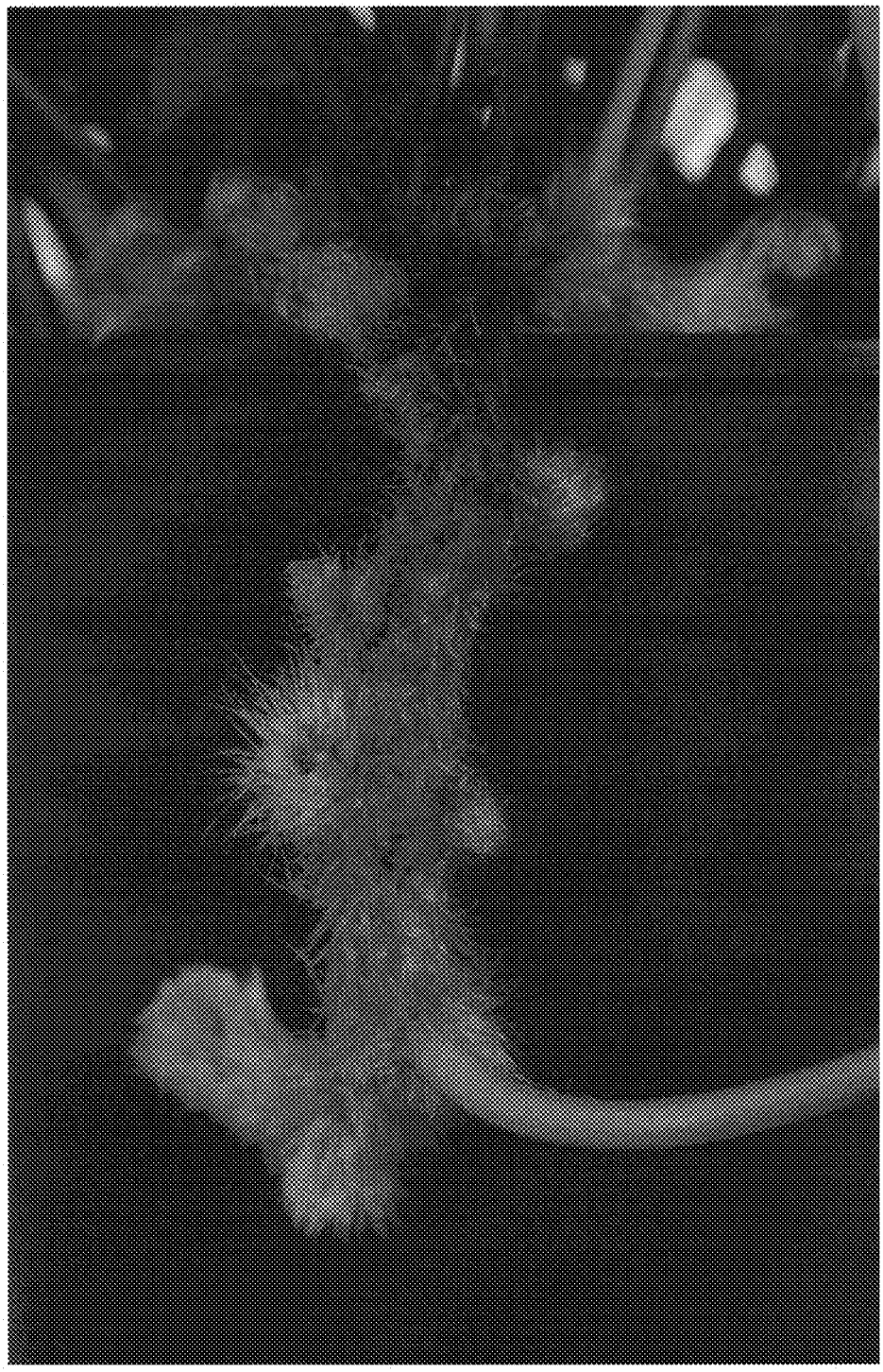
FIG. 3 illustrates, as nearly true as it is reasonably possible to make the same in color photographs of this type, the typical rhizomes of 'Nicolas Diamond'.

The following observations and measurements made in September of 2018 describe averages from a sample set of six specimens of 24 month old 'Nicolas Diamond' plants grown in 17 cm nursery containers at a greenhouse in Burgh Haamstede, the Netherlands. Plants were produced using conventional greenhouse production protocols which consisted of overhead irrigation and liquid fertilizer applications. No photoperiodic treatments or artificial light was given to the plants.

Those skilled in the art will appreciate that certain characteristics will vary with older or, conversely, with younger plants. 'Nicolas Diamond' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2015 (sixth edition).

A botanical description of 'Nicolas Diamond' and a comparison with the parent plants are provided below.

Plant description:

*Growth habit.*—Herbaceous perennial fern with an upright to arching growth habit; leaves growing from a basal rhizomes.

*Plant shape.*—Flattened globular.

*Height from soil level to top of foliar plane.*—53.0 cm.

*Plant spread.*—Average of 88.5 cm.

*Growth rate.*—Moderate.

*Plant vigor.*—Moderate to high.

*Propagation.*—Type — Mericloning. Crop time — Approximately 26 weeks from propagation to a marketable plant.

*Disease and pest resistance or susceptibility.*—Neither susceptibility nor resistance to pests and diseases common to either *Phlebodium aureum* or *Pyrrosia lingua* have been observed.

*Environmental tolerances.*—Adapt to, at least, USDA Zones 10 to 13 and temperatures as high as 35 degrees Celsius; high tolerance to rain; moderate tolerance to wind.

Root system:

*General.*—Creeping rhizomes which are densely covered with a soft pubescence.

*Length.*—7.8 cm.

*Diameter.*—0.8 cm.

*Texture.*—Densely pubescent; covered with a soft pubescence of hairy scales. The average length of scales is 0.9 cm.

*Color.*—Greyed-yellow, nearest to 161D; base of the hairy scales is greyed-orange, nearest to RHS 164A.

Fronds:

*Arrangement.*—Alternate; growing from creeping basal rhizomes.

*Attachment.*—Petiolate.

*Division.*—Simple.

*Dimensions.*—30.6 cm long and 18.2 cm wide, on average.

*Shape.*—Pinnatifid.

*Aspect.*—Flat with leaf apices curled downward at an average angle of 30 degrees to vertical.

*Attitude.*—At an average of 20 degrees to vertical at the base and arching to an average angle of 70 degrees to vertical.

*Apex.*—Emarginate or cleft.

*Base.*—Short attenuate.

*Margin.*—Deeply lobed with convergent sinuses; leaves are moderately undulate.

*Pubescence and texture and luster of adaxial surface.*—Glabrous, smooth, and glossy.

*Pubescence, texture and luster of abaxial surface.*—Glabrous and smooth, with the exception of the main vein at the base of the frond which is sparsely covered with curly hairs; hairs are 0.3 cm long on average and are colored greyed-brown, nearest to RHS 199A. The abaxial surface of the frond is moderately glossy.

*Color.*—Juvenile foliage, adaxial surface — Yellow-green, nearest to RHS 144A. Juvenile foliage, abaxial surface — Yellow-green, nearest to in between RHS 144A and 144B. Mature foliage, adaxial surface — Deep dark green; nearest to in between green, RHS NN137A, and yellow-green, RHS 146A. Mature foliage, abaxial surface — Green, nearest to RHS 137B.

*Venation.*—Pinnate.

*Venation color, adaxial surface.*—The main vein is yellow-green, nearest to RHS 146A, and is heavily suffused with brown towards the proximal end, nearest to in between RHS 200B. Secondary veins are green, nearest to RHS NN137A.

*Venation color, abaxial surface.*—The main vein is yellow-green, nearest to RHS 146A, and is heavily suffused with brown towards the proximal end, nearest to in between RHS 200B. Secondary veins are yellow-green, nearest to RHS 147A.

*Petiole.*—Length — 30.8 cm. Diameter — 0.35 cm. Strength — Strong. Pubescence, texture and luster — Glabrous, smooth, and glossy. Color, adaxial surface — Greyed-brown, nearest to a mixture of RHS N199B and N199C. Color, abaxial surface — Greyed-brown, nearest to in between RHS N199B and 200B.

Sori: No sori present.

COMPARISONS WITH THE PARENT PLANTS

Plants of the new cultivar 'Nicolas Diamond' differ from the seed parent, *Phlebodium aureum* 'Mandaianum' (unpatented), which is also the closest known commercial comparator, in the characteristics described in Table 1 below.

TABLE 1

| Characteristic | 'Nicolas Diamond' | 'Mandaianum' |
|---|---|---|
| Growth habit. | More arching than 'Mandaianum'. | More upright than 'Nicolas Diamond'. |
| General coloration of the mature foliage. | Darker green than 'Mandaianum'. | Lighter green than 'Nicolas Diamond'. |
| Length of mature foliage. | Longer than 'Mandaianum'. | Shorter than 'Nicolas Diamond'. |
| Foliage margins. | Deeply lobed; sinuses are not as deep or as wide as those of Mandaianurni. | Incised; sinuses are deeper and wider than those of 'Nicolas Diamond'. |

Plants of the new cultivar 'Nicolas Diamond' differ from the pollen parent, *Pyrrosia lingua* 'Cristata' (unpatented), in the following characteristics described in Table 2 below.

TABLE 2

| Characteristic | 'Nicolas Diamond' | 'Cristata' |
|---|---|---|
| General coloration of the adaxial surface of the mature foliage. | Darker green than 'Cristata'.. | Lighter green than 'Nicolas Diamond'. |
| Foliage apex. | Cleft. | Several times irregularly forked; i.e. crested. |
| Foliage aspect. | Flat with a downwardly curled apex. | Twisted with a heavily twisted apex. |
| Presence of sori. | No sori present. | Abaxial surface of the foliage is densely covered with sori. |

That which is claimed is:

1. A new and distinct variety of x *Phlebosia* plant named 'Nicolas Diamond', substantially as described and illustrated herein.

* * * * *